US008897418B2

(12) United States Patent
Hasegawa

(10) Patent No.: US 8,897,418 B2
(45) Date of Patent: Nov. 25, 2014

(54) X-RAY APPARATUS

(75) Inventor: Naoki Hasegawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 294 days.

(21) Appl. No.: 13/586,241

(22) Filed: Aug. 15, 2012

(65) Prior Publication Data

US 2014/0050300 A1 Feb. 20, 2014

(51) Int. Cl.
*H05G 1/64* (2006.01)
*H04N 5/32* (2006.01)
*G01N 23/04* (2006.01)

(52) U.S. Cl.
CPC ............. *H04N 5/3205* (2013.01); *G01N 23/04* (2013.01)
USPC .......................... 378/98.11; 378/98.12; 378/62

(58) Field of Classification Search
CPC ........ A61B 6/482; A61B 6/06; H04N 5/3205; G21K 1/025; G21K 1/10; G06T 7/0012; G06T 5/50
USPC ....................... 378/62, 98.11, 98.12, 154–160
See application file for complete search history.

(56) References Cited

U.S. PATENT DOCUMENTS

| 5,881,162 | A | 3/1999 | Ishimitsu |
| 7,424,138 | B2 | 9/2008 | Takagi |
| 2002/0131557 | A1 | 9/2002 | Goto |

FOREIGN PATENT DOCUMENTS

| JP | 06-164840 | | 6/1994 |
| JP | 08-88765 | A | 4/1996 |
| JP | 2002336220 | A | 11/2002 |
| JP | 2005-021334 | A | 1/2005 |

OTHER PUBLICATIONS

Japanese Notification of Reasons of Rufusal issued in Application No. JP2010-045340 dated Jul. 9, 2013.

*Primary Examiner* — Courtney Thomas
(74) *Attorney, Agent, or Firm* — McDermott Will & Emery LLP

(57) ABSTRACT

An X-ray apparatus includes a pixel-extracting section for extracting pixels determined in advance in each line of an image containing a grid moiré pattern, a FFT processing section for performing one-dimensional FFT to the extracted pixels, a peak-frequency detecting section for detecting a peak frequency from a frequency characteristic for each line having undergone FTT, a frequency-characteristic preparing section for preparing a frequency characteristic for extracting the grid moiré pattern in accordance with the detected peak-frequency, an inverse FFT processing section for performing inverse FFT to the frequency characteristic prepared by the frequency-characteristic preparing section, and an FIR filtering section for performing FIR filtering on the image with use of a value calculated by the inverse FFT processing section as an FIR filter coefficient.

8 Claims, 10 Drawing Sheets

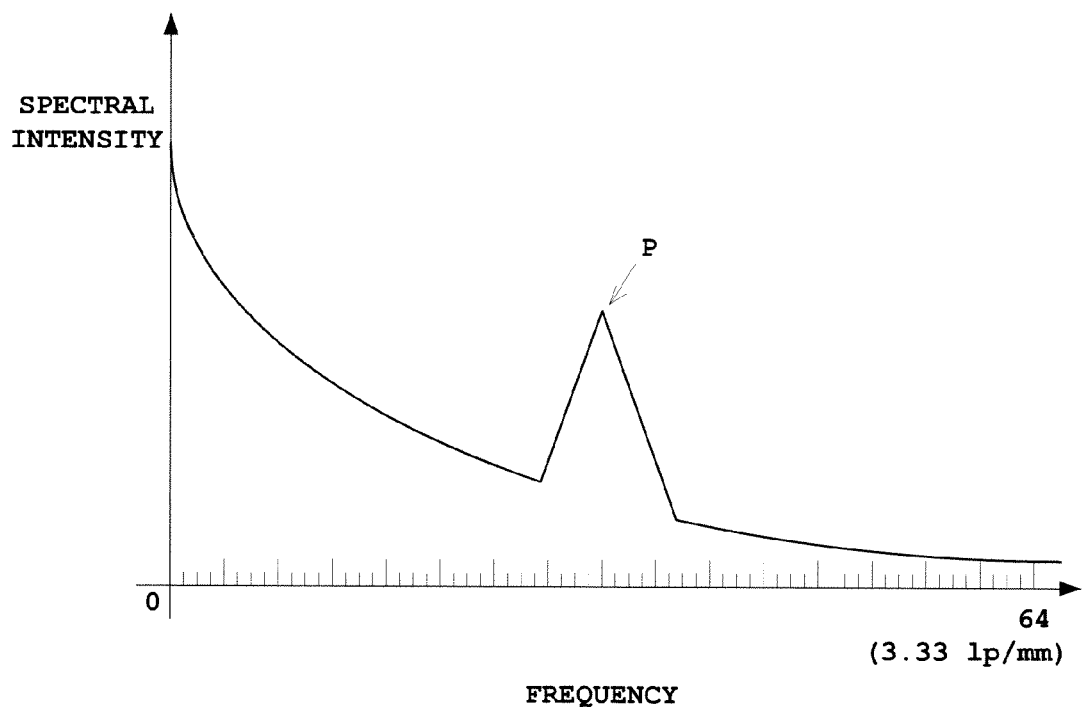

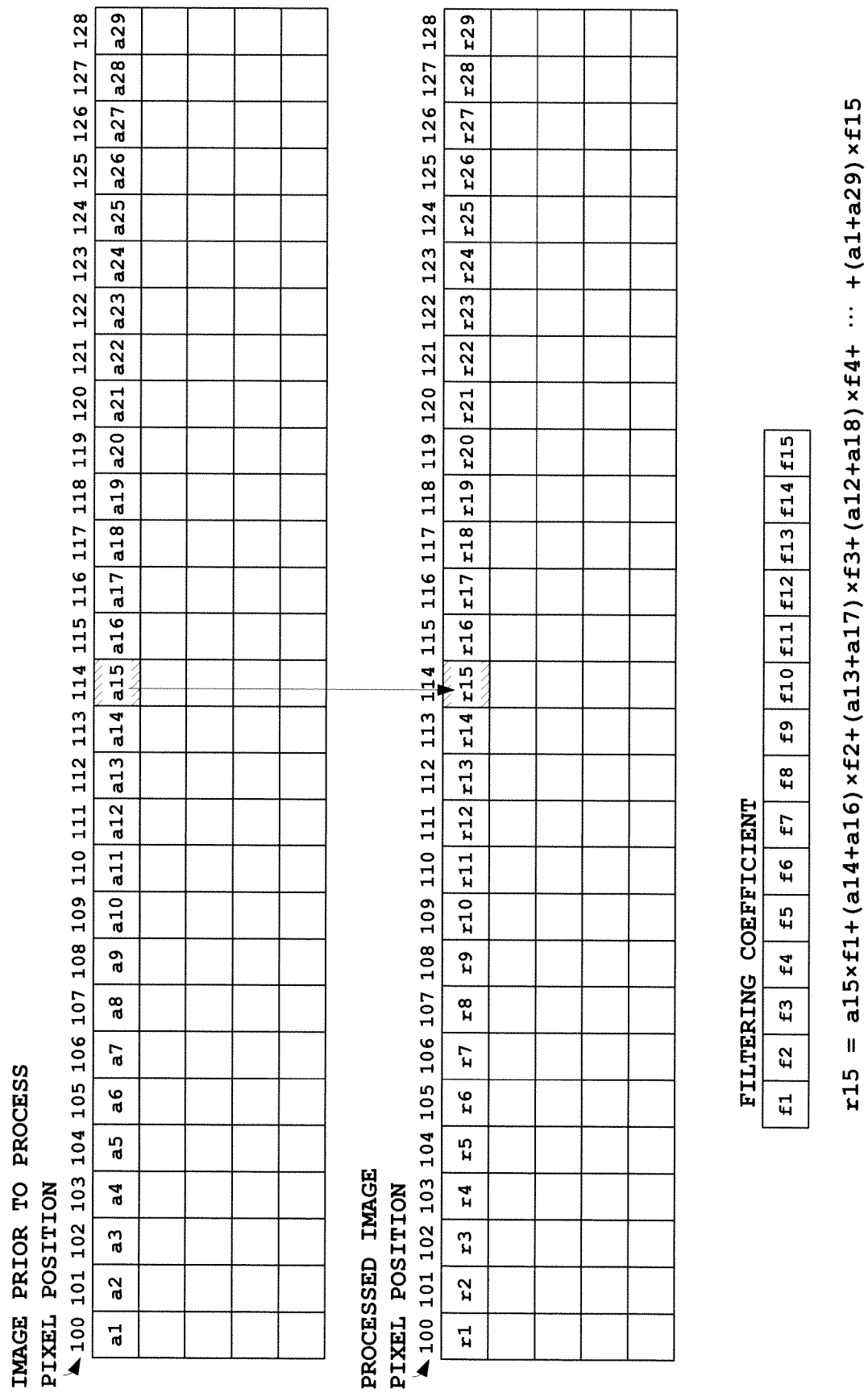

X-RAY APPARATUS

BACKGROUND OF THE INVENTION

1. Field of the Invention

This invention relates to an X-ray apparatus for use in the medical and industrial fields that includes an X-ray grid provided in an incidence surface side of an X-ray detector for removing scattered rays, the X-ray detector detecting X-rays emitted from an X-ray tube and transmitting through a subject. This invention is directed to a technique of removing a grid moiré pattern by the X-ray grid from an obtained image.

2. Description of the Related Art

Such conventional X-ray apparatus includes a top board for supporting a subject placed thereon, an X-ray tube for irradiating the subject with X-rays, an X-ray detector, such as a direct conversion type flat panel detector (FPD) for detecting X-rays transmitting through the subject M. The X-ray tube emits X-rays, and the X-ray detector detects an intensity distribution of the X-rays transmitting through the subject M. Thereby, X-ray fluoroscopy and radiography are conducted, through which fluoroscopic X-ray images are successively displayed as dynamic images on a display, such as a monitor.

Here, scattered rays occur when X-rays emitted from the X-ray tube transmit through the subject. The obtained image containing the scattered rays is to be blurred and unclear. Then the X-ray grid that removes scattered rays is arranged on an incidence surface side of the X-ray detector, thereby removing the scattered rays. The X-ray grid has an absorber (e.g., lead) for absorbing X-rays and a transparent body (e.g., aluminum or air) for transmitting X-rays, the absorbers and the transparent bodies being disposed alternately in parallel. Thus, the X-ray detector can detect only X-rays that transmit between the adjacent absorbers of the alternately disposed absorbers and transparent bodies, i.e. only X-rays that transmit along the transparent body between the absorbers. Consequently, a clear image having a higher contrast can be obtained.

On the other hand, a grid moiré pattern appears periodically in a fluoroscopic X-ray image having scattered rays removed therefrom by the X-ray grid due to differences between a sampling interval of the X-ray detector and an interval of the X-ray grid (an interval of the adjacent absorbers, or an interval of the adjacent transparent bodies). Various methods have been proposed conventionally for removing the grid moiré pattern (grid pattern). See, for example, Japanese Patent Publication No. 2005-21334A.

In Japanese Patent Publication No. 2005-21334A, applying different filters on each divided area of a radiation image can achieve suitable removal of the grid pattern from the radiation image. For example, a Gabor filter and a Wavelet filter are used for the filter.

Description will be given next of one example of the conventional methods of removing a grid moiré pattern by an X-ray grid with reference to FIGS. 1A through 1C and FIGS. 2A through 2C.

Now reference is made to FIG. 1A. FIG. 1A shows a fluoroscopic X-ray image obtained. An object to be observed is denoted by the symbol OB. A grid moiré pattern by an X-ray grid is denoted by the symbol G. Here, the grid moiré pattern appears such that lines extending vertically are arranged horizontally. An outer periphery of the fluoroscopic X-ray image is denoted by the symbol C by two-dot chain lines. Here, it is assumed that the X-ray detector detects X-rays transmitting through the subject and the X-ray grid using an image size of 2880×2880 pixels.

Firstly, one-dimensional Fast Fourier Transform (hereinafter, appropriately referred to as an "FFT") is performed on an image containing a grid moiré pattern by an X-ray grid (hereinafter, appropriately referred to as a "source image"), shown in FIG. 1A, for each one horizontal line from an upper portion of the image. At this time, the number of data points is 2880 pixels in one line. The FFT and inverse Fast Fourier Transform (hereinafter, appropriately referred to as an "inverse FFT") to be mentioned below are performed with powers-of-two number of data points. Thus, in order to calculate the number of data points of 2880 pixels through the FFT and the inverse FFT, powers-of-two number of data points including the number of data points of 2880 pixels are needed. Specifically, the number of data points of $2^{11}=2048$ does not satisfy the 2880 data points. That is, at least the number of data points of $2^{12}=4096$ is needed. One-dimensional FFT is performed for one line having the number of data points of 4096 points. Here, an example of one line to undergo FFT is denoted by the symbol L in FIG. 1A.

Next reference is made to FIG. 2A. FIG. 2A shows a frequency characteristic indicating the result of the one-dimensional FFT for one horizontal line in the source image. A peak frequency of the grid moiré pattern by the X-ray grid is detected for each line, as denoted by the symbol P in FIG. 2A, using a frequency characteristic of each line having undergone the FFT.

Next reference is made to FIG. 2B. A frequency characteristic for extracting grid moiré pattern components from the source image is prepared based on the detected peak frequency. The frequency characteristic is prepared with the number of data points of 2048 in accordance with the frequency characteristic shown in FIG. 2A.

Masking (filtering) of the frequency characteristic, shown in FIG. 2A, for each line having undergone one-dimensional FFT from the upper portion of the source image is performed with the frequency characteristic, shown in FIG. 2B, that are prepared based on the peak frequency. Specifically, calculation is performed through multiplying the frequency characteristic of FIG. 2A by that of FIG. 2B. Thereby, only frequency components of the grid moiré pattern as shown in FIG. 2C are to be extracted.

One-dimensional inverse FFT is performed to the frequency characteristic of only the grid moiré pattern components for each line having undergone masking, as shown in FIG. 2C. Thereby, a grid moiré pattern image as denoted by the symbol G' in FIG. 1B is to be prepared. In this case, the inverse FFT is performed with the number of data points 4096 that is obtained through adding folding components to the number of data points 2048 for the frequency characteristic with the grid moiré pattern for each line having undergone masking being extracted.

Then, the grid moiré pattern image shown in FIG. 1B that is prepared through the inverse FFT is subtracted from the source image shown in FIG. 1A, whereby the grid moiré pattern is removed from the source image. FIG. 1C shows an image with the grid moiré pattern removed therefrom.

As mentioned above, when the X-ray detector has an image size of 2880 by 2880 pixels, for example, FFT and inverse FFT are performed with use of at least the number of data points of $2^{12}=4096$. Thereby, the grid moiré pattern for removal from the source image is generated.

The conventional example as above has the following drawback. Specifically, where an image process, such as fluoroscopy, has to be performed in real time, an image process such as preparing and removing a grid moiré pattern is not performed in software. In other words, the same processing is mounted on hardware, such as an FPGA (Field Programmable Gate Array), and the hardware is incorporated into the apparatus. Here, the hardware enables performance at a higher speed than the software. On the other hand, where image resolution, i.e., a pixel number is large, a calculation amount required for Fast Fourier Transform becomes extremely large. Thus, there may arise a drawback that an amount of logic and computation time necessary for hardware, such as an FPGA, increases.

For instance where the FFT is performed to data of 2880 pixels for one line, calculation requires powers-of-two number of data points including the number of data points of 2880 pixels, i.e., 4096 points. Therefore, large-scale calculation is to be needed. In this case, for example, calculation of the image for one line (2880 pixels) needs more time than that for input into hardware, such as the FPGA. As a result, it becomes impossible to perform an image process in real time. Thus an image process with hardware such as the FPGA cannot be achieved.

SUMMARY OF THE INVENTION

This invention has been made regarding the state of the art noted above, and its object is to provide an X-ray apparatus that can generate a grid moiré pattern image same as the conventional at a less calculated amount than the conventional.

Additional features of the invention will be set forth in the description which follows, and in part will be apparent from the description, or may be learned by practice of the invention.

This invention is constituted as stated below to achieve the above object. One example of this invention discloses an X-ray apparatus with an X-ray irradiation section for irradiating a subject with X-rays, an X-ray detector for detecting X-rays transmitting through the subject, and an X-ray grid disposed on an incidence surface side of the X-ray detector for removing scattered rays. The apparatus includes a pixel extracting section for extracting pixels determined in advance in each line perpendicular to a grid moiré pattern of an image, the grid moiré pattern by the X-ray grid being contained in the image; a Fast Fourier Transform processing section for performing one-dimensional Fast Fourier Transform to the pixels extracted by the pixel extracting section; a peak-frequency detecting section for detecting a peak frequency from a frequency characteristic for each line calculated by the Fast Fourier Transform processing section, the peak frequency being a frequency component of the grid moiré pattern; a frequency-characteristic preparing section for preparing a frequency characteristic for extracting a grid moiré pattern image in accordance with the peak-frequency detected by the peak-frequency detecting section; an inverse Fast Fourier Transform processing section for performing inverse Fast Fourier Transform to the frequency characteristic prepared by the frequency-characteristic preparing section; and an FIR filtering section for performing FIR filtering on the image with use of a value calculated by the inverse Fast Fourier Transform processing section as an FIR filter coefficient.

According to the X-ray apparatus in one example of the invention, the Fast Fourier Transform processing section performs one-dimensional Fast Fourier Transform to the pixels in each line extracted by the pixel extracting section in the image having the grid moiré pattern contained therein. Subsequently, the peak-frequency detecting section detects a peak frequency from the frequency characteristic for each line calculated through Fast Fourier Transform, the peak frequency being a frequency component of the grid moiré pattern. Then a frequency characteristic for extracting the grid moiré pattern is prepared in accordance with the peak frequency detected by the peak-frequency detecting section. Then the inverse Fast Fourier Transform processing section performs inverse Fast Fourier Transform to the frequency characteristic to calculate an FIR filtering coefficient. Thereafter, the FIR filtering section performs FIR filtering on the image having the grid moiré pattern contained therein. Thereby a grid moiré pattern image for removing the grid moiré pattern can be generated.

Thereby, calculations through one-dimensional Fast Fourier Transform and inverse Fourier transform are performed not for the entire of each line but for a part of each line. That is, the Fast Fourier Transform processing section and the inverse Fast Fourier Transform processing section can perform a reduced calculation amount of Fast Fourier Transform and inverse Fast Fourier Transform. As a result, a reduced calculation amount can be achieved when an image process of extracting a grid moiré pattern image extraction is mounted on hardware, such as the FPGA. Thus, an amount of logic and computation time necessary for hardware, such as the FPGA, can be reduced. In addition, the grid moiré pattern image in the entire source image can be extracted through calculating an FIR filter coefficient from a part of pixels extracted in each line and using the coefficient in the FIR filtering process.

Moreover, the pixel extracting section in the foregoing X-ray apparatus preferably extracts powers-of-two number of pixels. Thereby an efficient calculation can be achieved upon performance of Fast Fourier Transform and inverse Fourier transform. For instance, the pixel extracting section extracts 200 pixels for one line, powers-of-two number of data points including the 200 pixels are needed for Fast Fourier Transform and inverse Fourier Transform. That is, data points of $2^8=256$ are needed. Thus total 56 data points are needed in addition to the 200 pixels to be extracted.

Moreover, the frequency-characteristic preparing section in the foregoing X-ray apparatus preferably prepares a frequency characteristic using powers-of-two number of data points. Thereby an efficient calculation can be achieved upon performance of inverse Fourier Transform. In addition, a more reduced calculation amount can be achieved when a frequency characteristic is prepared using the data points having a fewer number than the pixels extracted by the pixel extracting section.

Moreover, the foregoing X-ray apparatus preferably includes a subtracting section for removing the grid moiré pattern image extracted by the FIR filtering section from the image. Thereby the grid moiré pattern image can be removed from the image containing the grid moiré pattern at a higher speed using the grid moiré pattern image extracted at a higher speed due to a reduced calculation amount (computation time) as conventional.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

FIG. 7 is a view of a frequency characteristic after Fast Fourier Transform.

FIG. 10 is a view provided for explanation of FIR filtering.

DESCRIPTION OF THE PREFERRED EMBODIMENTS

Figure 1A:
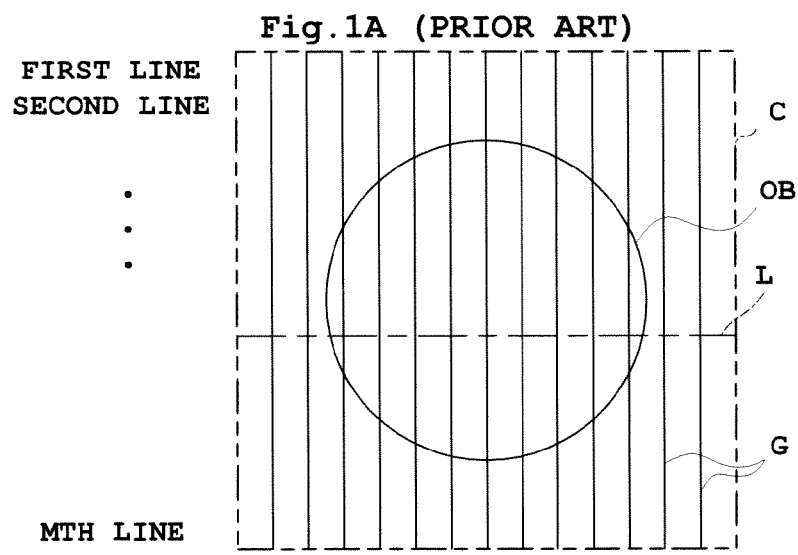
FIG. 1A is a view with respect to explanation of operation of a conventional example showing an image containing a grid moiré pattern (source image).
Figure 1B:
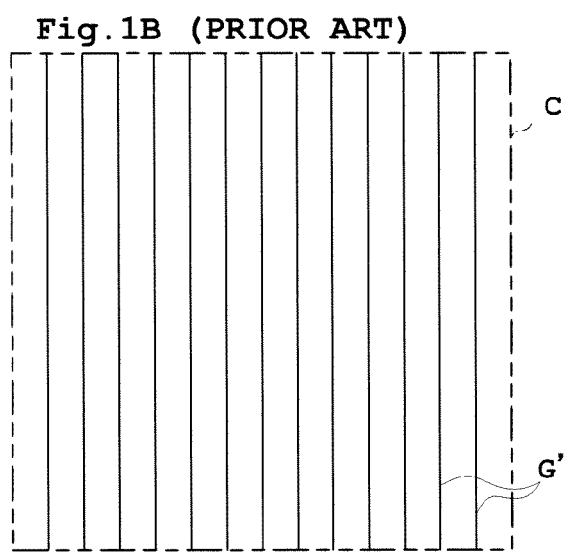
FIG. 1B is a view with respect to explanation of operation of the conventional example showing a grid moiré pattern image extracted from the source image.
Figure 1C:
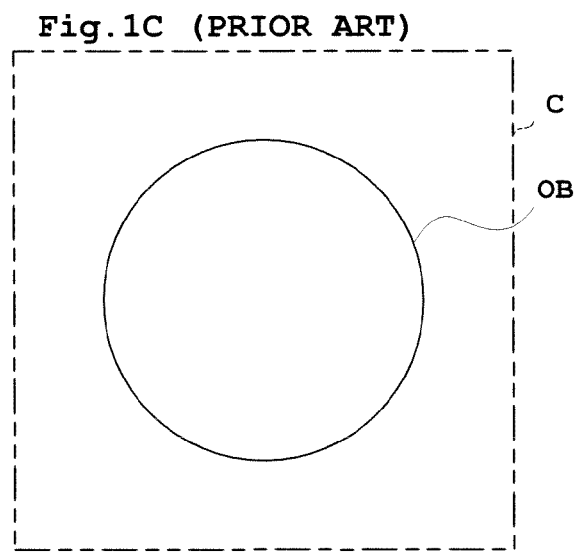
FIG. 1C is a view with respect to explanation of operation of the conventional example showing an image having the grid moiré pattern removed therefrom.
Figure 2A:
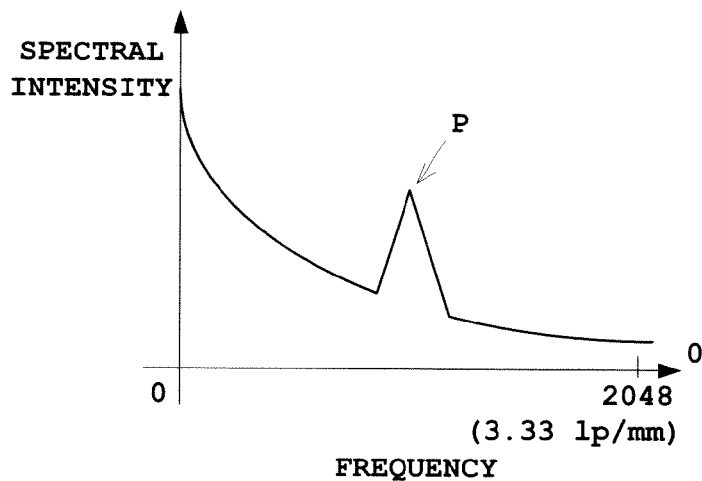
FIG. 2A is a view with respect to explanation of operation of the conventional example showing a frequency characteristic after Fast Fourier Transform.
Figure 2B:
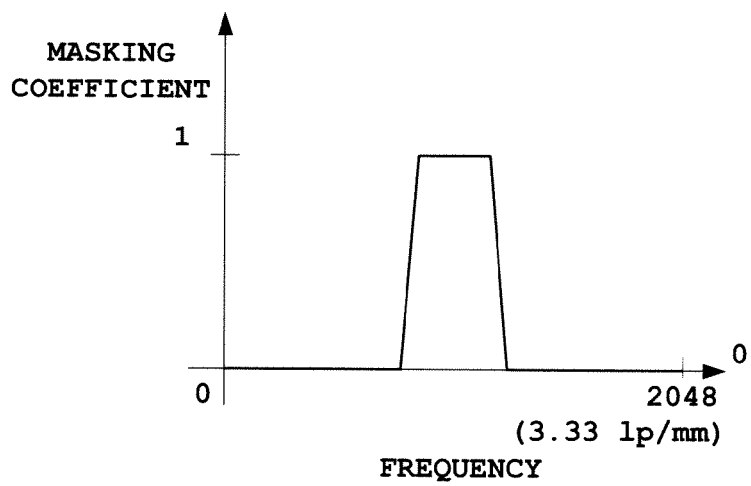
FIG. 2B is a view with respect to explanation of operation of the conventional example showing a frequency characteristic prepared for masking.
Figure 2C:
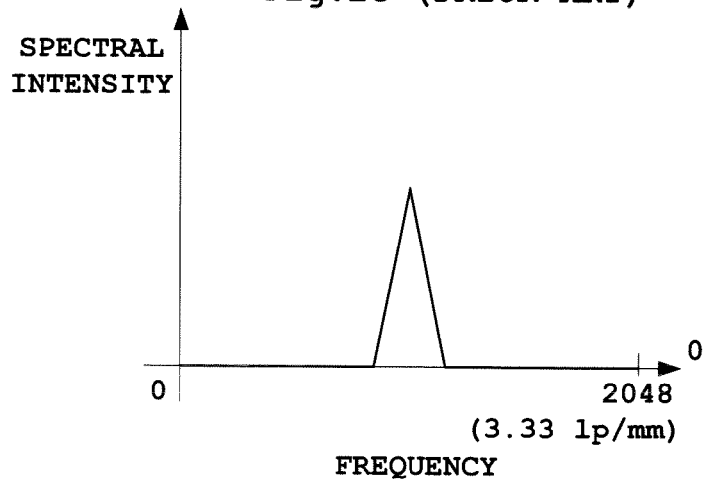
FIG. 2C is a view with respect to explanation of operation of the conventional example showing a frequency characteristic with only grid moiré pattern components after masking.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

A preferred example of this invention will be described in detail hereinafter with reference to the drawings.

Figure 3:
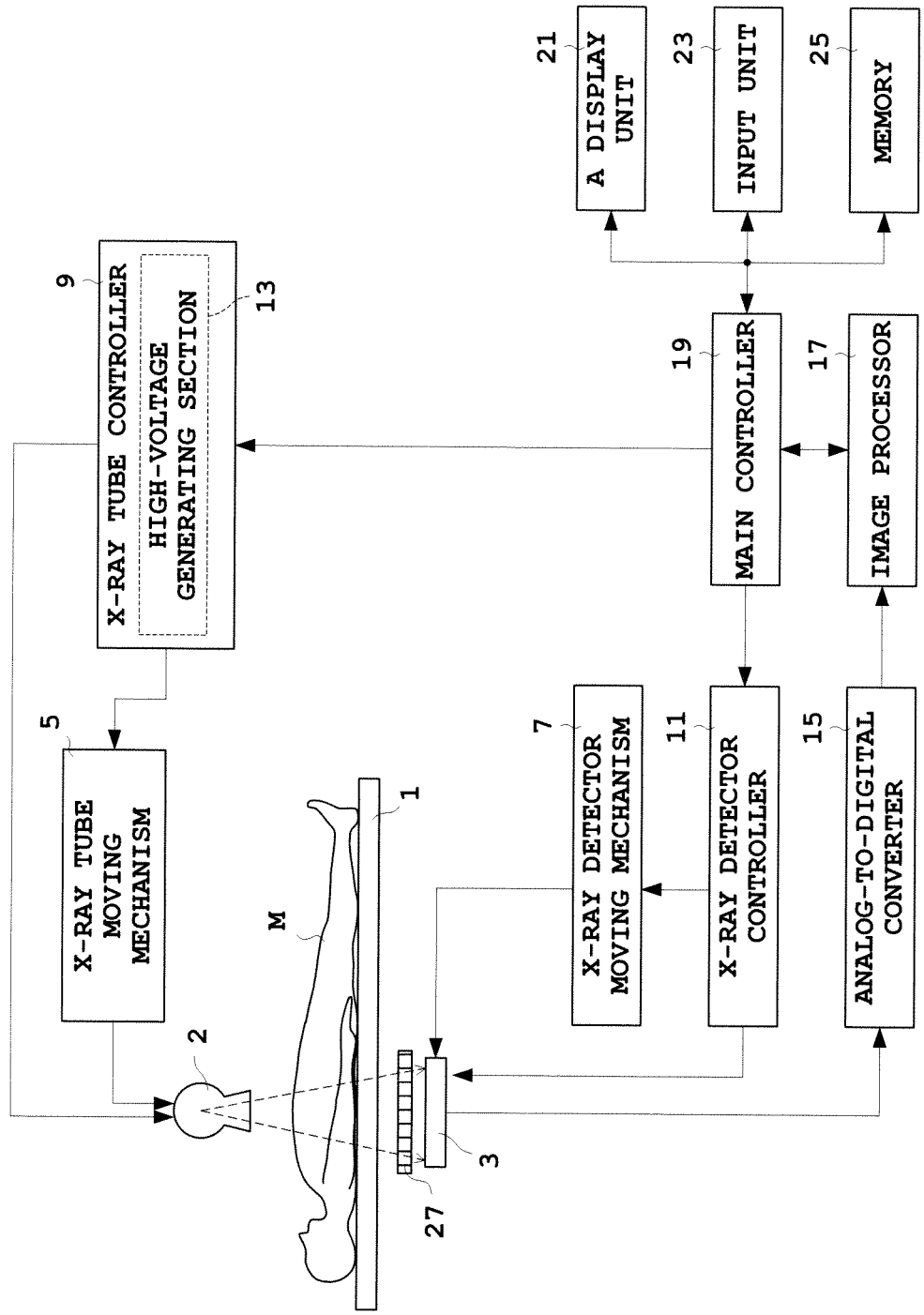
FIG. 3 is a block diagram showing an X-ray apparatus according to one example.

FIG. 3 is a block diagram showing an overall construction of an X-ray apparatus according to one example of the invention.

Now reference is made to FIG. 3. An X-ray apparatus includes a top board 1 for supporting a subject M placed thereon, an X-ray tube 2 for irradiating the subject M with X-rays, and a flat panel detector (hereinafter, appropriately referred to as an "FPD") 3 for detecting X-rays transmitting through the subject M. Here, the X-ray tube 2 corresponds to the X-ray irradiation section in the example of this invention. The FPD 3 corresponds to the X-ray detector in the example of this invention.

Moreover, the X-ray apparatus further includes an X-ray tube moving mechanism 5 for moving the X-ray tube 2, and an X-ray detector moving mechanism 7 for moving the FPD 3. The X-ray tube moving mechanism 5 and the X-ray detector moving mechanism 7 are controlled by an X-ray tube controller 9 and an X-ray detector controller 11, respectively. The X-ray tube controller 9 includes a high-voltage generating section 13 that generates a tube voltage and a tube current in the X-ray tube 2.

The X-ray tube controller 9 executes control to the X-ray tube 2 necessary for X-ray irradiation in accordance with irradiation conditions, such as a tube voltage and a tube current, determined in advance by an input unit (23), which is to be mentioned later. The X-ray tube controller 9 controls scanning movement through moving the X-ray tube 2 horizontally or rotationally moving the X-ray tube 2 about a body axis of the subject M. The X-ray tube controller 9 also controls setting of an irradiation filed of a collimator (not shown) disposed on an X-ray tube 2 side. The X-ray detector controller 11 controls scanning movement through moving the FPD 3 horizontally or through rotationally moving the FPD 3 about the body axis of the subject M. In time of scanning movement, the X-ray tube 2 and the FPD 3 move while facing each other such that the FPD 3 can detect X-rays emitted from the X-ray tube 2.

Moreover, the X-ray apparatus also includes an analog-to-digital converter 15 for digitizing X-ray detection signals as charge signals from the FPD 3 and fetching the X-ray detection signals, and an image processor 17 for performing various processes based on the X-ray detection signals outputted from the analog-to-digital converter 15. Furthermore, the X-ray apparatus includes a main controller 19 for performing an overall control of each component in the X-ray apparatus, a display unit 21 composed of a monitor and others for displaying processed fluoroscopic X-ray images, an input unit 23 that allows an operator to input various settings, and a memory 25 for storing the processed fluoroscopic X-ray images.

The analog-to-digital converter 15 converts charge signals outputted from the FPD 3 from analog values into digital values. Then the analog-to-digital converter 15 outputs the digitized X-ray detection signals. The main controller 19 is composed of a central processing unit (CPU) and others, and performs an overall control for operating the entire apparatus suitably. The input unit 23 is composed of a mouse, a keyboard, and others. The memory 25 is composed of a storage medium represented by such as a ROM (Read-only Memory), and RAM (Random-Access Memory). In the X-ray apparatus, the FPD 3 firstly detects X-rays transmitting through the subject M, and then the image processor 17 performs an image process based on intensity distributions of the detected X-rays. The display unit 21 displays the processed fluoroscopic X-ray images. Thereby radiography and X-ray radioscopy of the subject M are performed.

The X-ray apparatus further includes an X-ray grid 27 on an incidence surface side of the FPD 3 for removing scattered rays. The X-ray grid 27 is composed of lead and aluminum, for example, alternately arranged.

<Image Processor>

Figure 4:
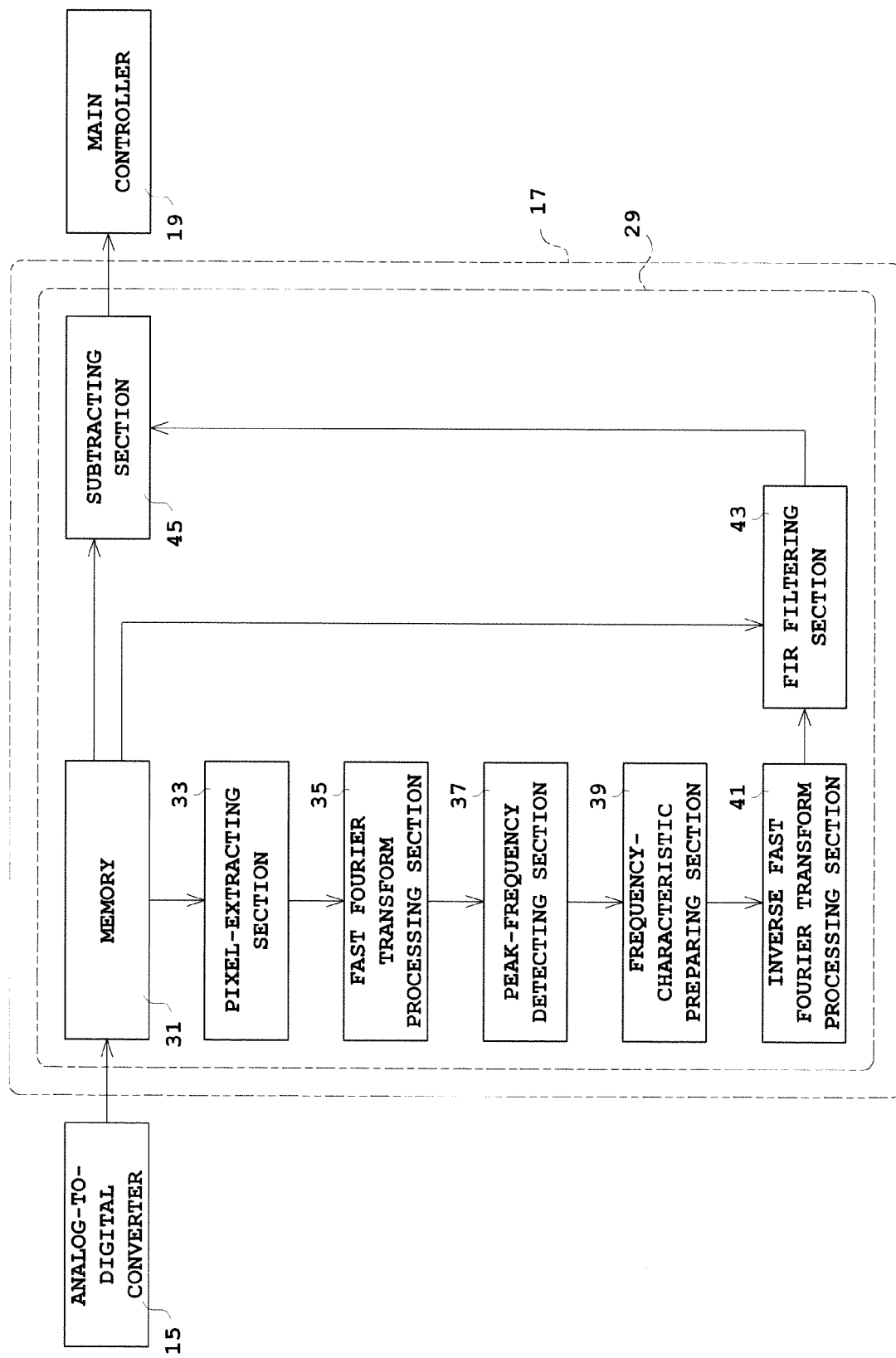
FIG. 4 is a block diagram showing an image processor according to the example.

Now reference is made to FIG. 4. FIG. 4 is a block diagram showing an image processor according to the example.

The image processor 17 is provided with a moiré-pattern removing section 29 for removing grid moiré patterns by the X-ray grid 27. The moiré-pattern removing section 29 includes a memory 31, a pixel extracting section 33, a Fast Fourier Transform processing section (hereinafter, appropriately referred to as an "FFT processing section") 35, a peak-frequency detecting section 37, a frequency-characteristic preparing section 39, an inverse Fast Fourier Transform processing section (hereinafter, appropriately referred to as an "inverse FFT processing section") 41, an FIR filtering section 43, and a subtracting section 45.

Figure 6A:
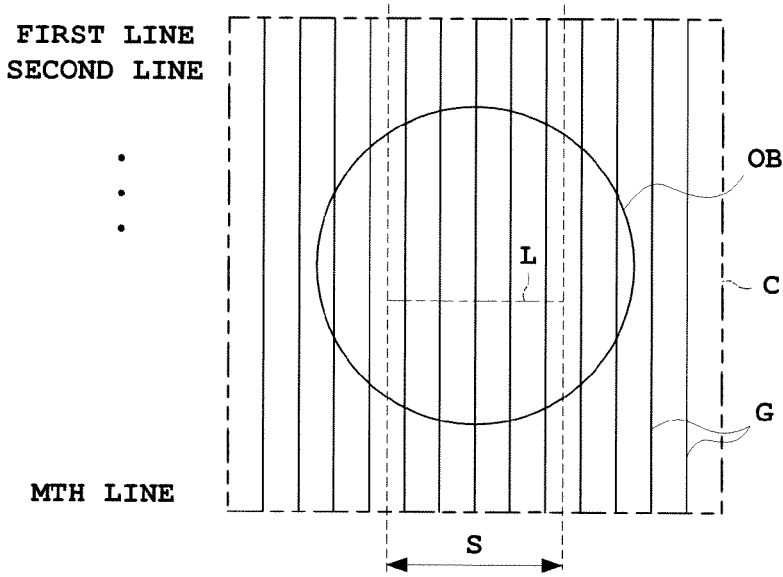
FIG. 6A is a view with respect to explanation of operation of the example showing an image containing a grid moiré pattern (source image).

The memory 31 memorizes fluoroscopic X-ray images as X-ray detection signals that are converted into digital signals by the analog-to-digital converter 15. That is, the memory 31 stores the image (source image) containing the grid moiré pattern by the X-ray grid 27. As shown in FIG. 6A, the pixel extracting section 33 extracts a given number of pixels in a given position for each horizontal line in the source image (symbol S) read out from the memory 31. For instance, when the FPD 3 is formed by 2880×2880 pixels, 128 pixels at the center of each horizontal line are to be extracted in order from the upper of the source image. The given position and the given number of pixels extracted from the source image are set in advance such that an effecting process can be achieved, and are inputted by the input unit 23. Moreover, the given number of pixels extracted from the source image is set by powers-of-two number of data points so as to be calculated by an FFT processor 35, which is to be mentioned later. Here in FIGS. 6A through 6C, an object to be observed is denoted by the symbol OB as mentioned above. The grid moiré pattern by the X-ray grid is denoted by the symbol G. The outer periphery of the fluoroscopic X-ray image is denoted by the symbol C by two-point chain dashes.

The FFT processor 35 performs one-dimensional Fast Fourier Transform (hereinafter, appropriately referred to as an "FFT") to the given number of pixels extracted by the pixel extracting section 33. That is, the FFT processor 35 performs one-dimensional FFT to the given number of pixels for each horizontal line from the upper of the source image. Here as shown by the symbol L in FIG. 6A, FFT is performed approximately perpendicularly to the lines extending in the longitudinal direction of the grid moiré pattern. The peak-frequency detecting section 37 detects a peak frequency as a frequency component of the grid moiré pattern in each line using the frequency characteristic for each line calculated by the FFT processor 35 through one-dimensional FFT. The peak-frequency detecting section 37 determines a representative value of the peak frequency based on the peak frequency detected in each line.

The frequency-characteristic preparing section 39 prepares a frequency characteristic for extracting the grid moiré pattern in accordance with the peak frequency detected by the peak-frequency detecting section 37. The frequency characteristic is prepared using powers-of-two number of data points that is equal to or fewer than the number of pixels extracted by the pixel extracting section 33. The number of data points is set in advance such that an effecting process can be achieved, and is inputted by the input unit 23 and the like. The inverse FFT processor 41 performs one-dimensional inverse Fast Fourier Transform to the frequency characteristic prepared by the frequency-characteristic preparing section 39.

Figure 6B:
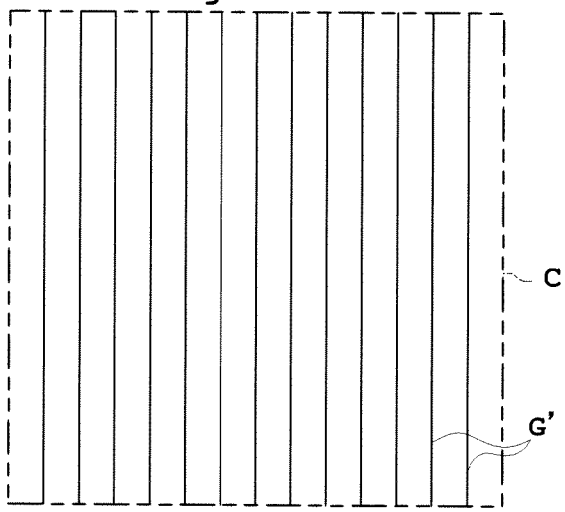
FIG. 6B is a view with respect to explanation of operation of the example showing a grid moiré pattern image extracted from the source image.

The FIR filter processor 43 performs FIR (Finite Impulse Response) filtering on the source image read out from the memory 31 with use of the value calculated by the inverse Fast Fourier Transform processor 41 as an FIR filter coefficient. Thereby, as shown in FIG. 6B, a grid moiré pattern image (symbol G') is extracted from the source image. The subtracting section 45 subtracts the grid moiré pattern image extracted by the FIR filtering section 43 from the source image, thereby removing the grid moiré pattern from the source image.

The image processor 17 includes, besides the moiré-pattern removing section 29, elements needed for an image process on an analog-to-digital converter 15 side or a main controller 19 side shown in FIG. 3. Examples of the element include a defective-pixel detecting section (not shown) for detecting defective pixels and a defective-pixel interpolating section (not shown) for interpolating the defective pixels detected by the defective-pixel detecting section.

Figure 5:
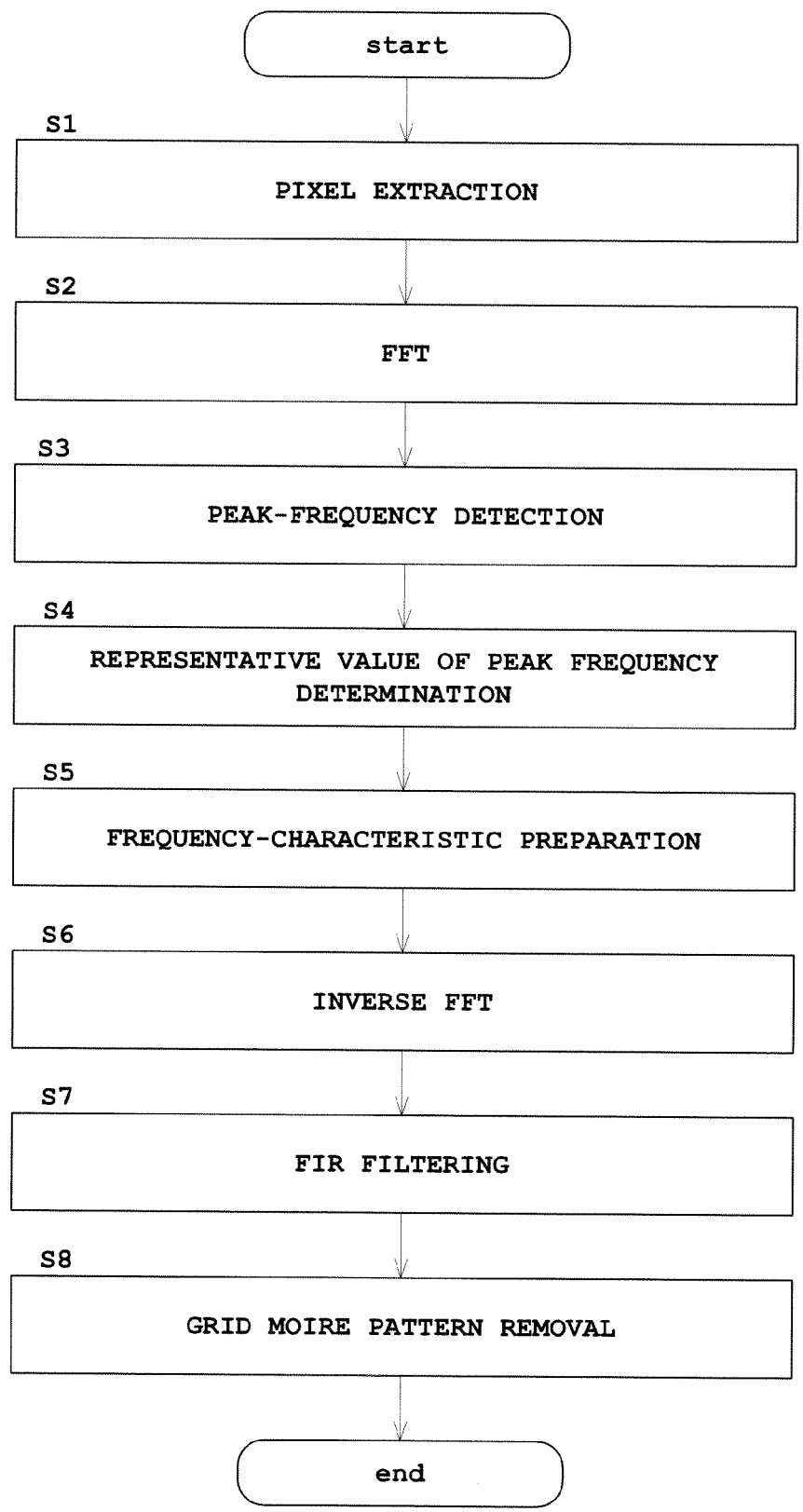
FIG. 5 is a flow chart provided for explanation of operations of the example.

Next, description will be given to one example of operations with a flow chart shown in FIG. 5. Additionally, reference will be made appropriately to FIGS. 6A through 10 as required. Herein, the description will be made from the step of reading an image containing a grid moiré pattern stored in the memory 31 and extracting pixels by the pixel extracting section 33 to the step of removing the grid moiré pattern from the source image by the subtracting section 45. Herein in Step S1 through Step S6, an FIR filter coefficient used with the FIR filtering in Step S7 is determined. Moreover, in the description, the FPD 3 has a pixel size of 2880×2880 pixels as one example.

[Step S1]

The image containing the grid moiré pattern stored in the memory 31 (source image) is read out, and the pixel extracting section 33 extracts a given number of pixels in a given position for each horizontal line in the source image. For instance, as shown in FIG. 6A, 128 pixels at the center of each horizontal line are extracted from the upper of the source image. Here, one example of extracting a given number of pixels in a given position of one line is denoted as the symbol L in FIG. 6A.

[Step S2]

The FFT processor 35 performs one-dimensional FFT to the extracted 128 pixels at the center of the source image obtained through extracting each horizontal line from the upper of the source image. FFT is performed based on the following Equations (1) and (2). Here in Equations (1) and (2), a pixel value of the source image is denoted by x(n), and a pixel value after FFT is denoted by X(n). In addition, a pixel position is denoted by n, and a pixel size of the image is denoted by N.

$$X(n) = \sum_{n=0}^{N-1} x(n) W^{kn} \quad (1)$$

$$W \equiv e^{j \times (2\pi/N)} = \cos(2\pi/N) + j \times \sin(2\pi/N) \quad (2)$$

The number of data points after FFT is to be 64 points that are a half of 128 points. That is because remaining half 64 points will appear as folding components having reverses orders of effective data.

[Step S3]

The peak-frequency detecting section 37 detects a peak frequency of the grid moiré pattern in each line using frequency characteristics having undergone FFT, as shown by the symbol P in FIG. 7. It is estimated that a detection range of the peak frequency appears within a specific range in accordance with a density of the X-ray grid 27 (lp/cm) and a pixel pitch of the FPD 3 (sampling frequency). For instance, when the X-ray grid 27 has a density of 50 [lp/cm](errors of +10%), a peak of the grid moiré pattern appears within a range of 1.25 [lp/mm] to 2.24 [lp/mm]. As shown in FIG. 7, the peak-frequency detecting section 37 detects a frequency with the maximum spectral intensity from the specific range where it is estimated that the peak of the grid moiré pattern appears. Detection is performed to the lines in order of FTT by the FFT processor 35, i.e., to the first line, the second line, . . . and the Mth line, from the upper of the source image. For instance, when the FPD 3 has 2880×2880 pixels, detection is performed from the first line to the 2880th line.

[Step S4]

The peak-frequency detecting section 37 determines a representative value of the peak frequency based on the peak frequency detected in each line. For instance, the value of the peak frequency where the peak frequency is checked in order of FFT and the same peak frequency is detected for six lines may be determined (fixed) as a representative value of the peak frequency. This method is not limitative. For instance, an average of the peak frequencies for all lines may be determined as a representative value of the peak frequency. Moreover, extraction is made to not only all lines but also a given number of lines, and then an average of the peak frequencies for the given number of lines may be determined as a representative value of the peak frequency.

[Step S5]

A frequency characteristic for extracting the grid moiré pattern from the source image is prepared in accordance with the representative value of the peak frequency detected by the peak-frequency detecting section 37. For instance, the frequency characteristic is prepared by 16 points. Next, description will be given of one example of a method for preparing a frequency characteristic for extraction of the grid moiré pattern.

Figure 8A:
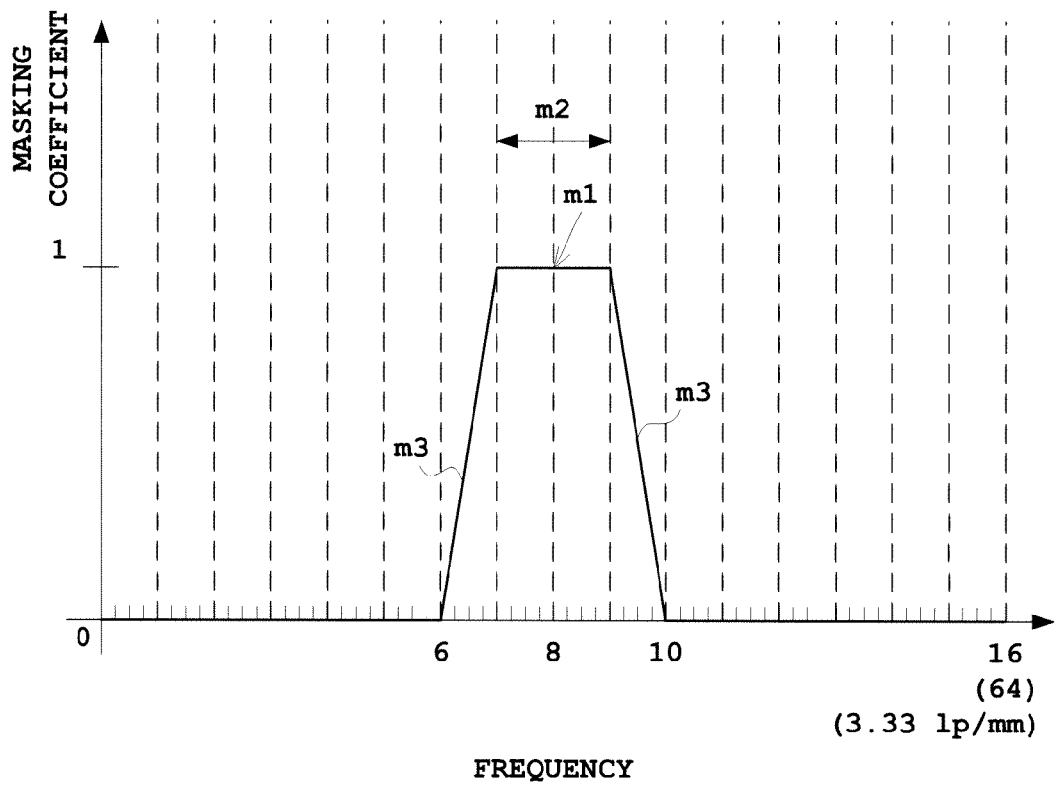
FIG. 8A is a view of a frequency characteristic having the eighth point as a center thereof for extracting the grid moiré pattern.
Figure 8B:
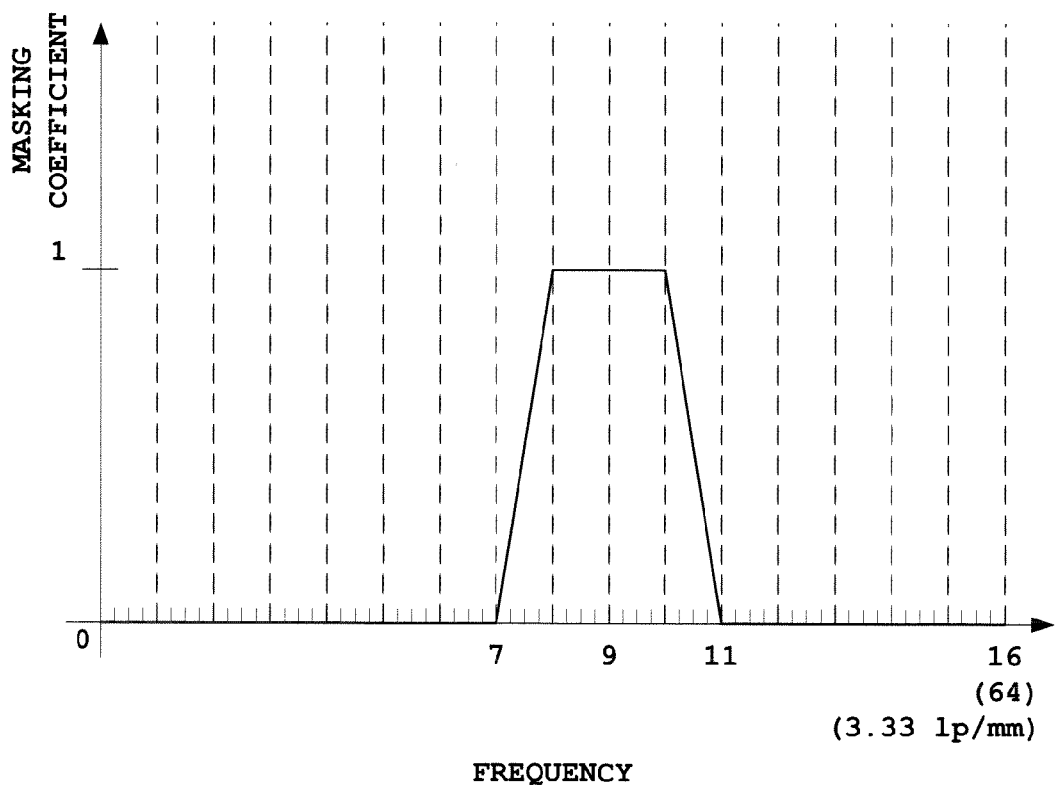
FIG. 8B is a view of the frequency characteristic having the ninth point as a center thereof for extracting the grid moiré pattern.

First, FFT is performed on each line of the source image. Thereafter, when it is determined which frequency in the frequency characteristic expressed with the number of 64 data points is a representative value of the peak frequency, a frequency characteristic expressed with 16 data points is prepared. The distribution of 16 points is fixed. Specifically, a peak frequency by 16 points (center position) varies in accordance with a position of the peak frequency determined by 64 points. For instance, as shown in FIG. 8A, where the peak frequency is in a range of 32th to 35th points, calculation is given of 32/64×16=8. Thereby, a frequency characteristic having the 8th point as a center thereof is to be prepared. Likewise, as shown in FIG. 8B, where the peak frequency is in a range of 36th to 39th points, calculation is given of 36/64×16=9. Thereby, a frequency characteristic having the 9th point as a center thereof is to be prepared.

A width (pass band) of ±0.2 [lp/mm] is provided at the center of the peak frequency converted into 16 points (a center position). That is, for the frequency characteristic by 16 points as shown in FIG. 8A, a range from 7th to 8th points and that from 8th to 9th points correspond to a width of ±0.2 [lp/mm]. Moreover, in FIG. 8B, a range from 8th to 10th points corresponds to a width of ±0.2 [lp/mm]. Here, the value of ±0.2 [lp/mm] indicates variations due to manufacturing errors of grid intervals in the X-ray grid 27.

Moreover, when a specific frequency band (frequency characteristic) is cut with a sharp filter, noises appear in the image having undergone an FIR filtering mentioned below. As the countermeasure, for example, slopes are provided in FIG. 8A from the 6th to 7th points and also from the 9th to 10th points. Likewise, in FIG. 8B, slopes are provided from the 7th to 8th points and from the 10th to 11th points.

As above, the frequency characteristic for extracting the grid moiré pattern can be prepared. For instance, as shown in FIG. 8A, a width m2 (from the 7th to the 9th points) is provided having a center position m1 of the peak frequency (the 8th point) where a masking coefficient is 1, the width m2 indicating variations due to manufacturing errors of the grid intervals in the X-ray grid 27. Then slopes m3 (from the 6th to 7th points and the 9th to 10th points) are provided on both ends of the width m2 such that a masking coefficient gently becomes 0. A masking coefficient is assumed 0 in a range other than the width m2 including the position m1 of the peak frequency, and the slopes m3 (i.e., a range larger than the 10th point and a range smaller than the 6th point).

[Step S6]

Figure 9:
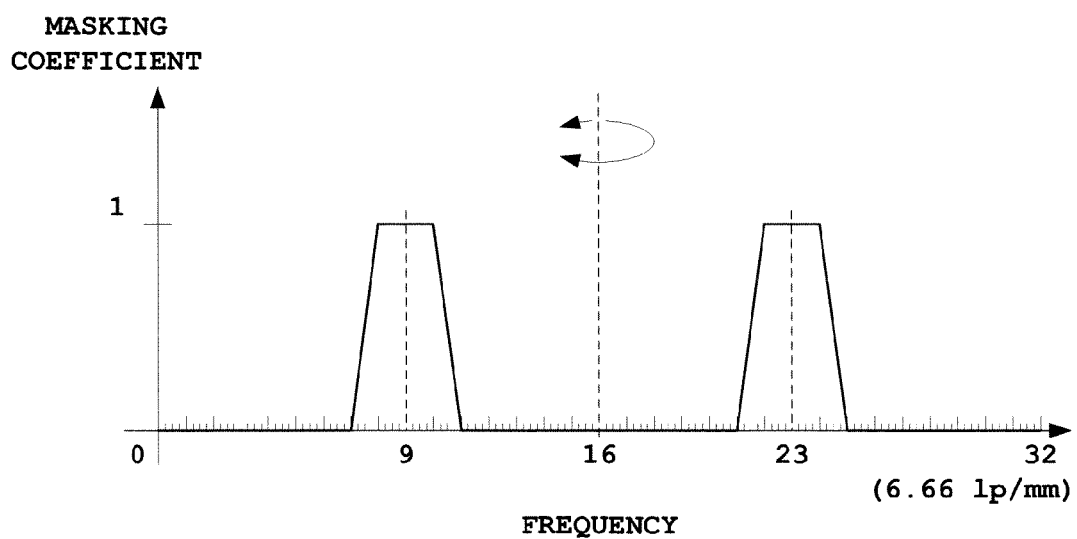
FIG. 9 is a view of a frequency characteristic prior to inverse Fast Fourier Transform.

The inverse FFT processor 41 performs inverse Fast Fourier Transform on the frequency characteristic for extracting the grid moiré pattern. Thereby, an FIR filter coefficient for preparing a grid moiré pattern image is substantially determined. The inverse FFT is performed with the number of data points obtained through adding folded components to the frequency characteristics for extracting the grid moiré pattern. For instance, for the frequency characteristic of 16 points, data of 16 points having the reversed order of the frequency characteristic of 16 points is added to be 32 points, where one-dimensional inverse Fourier Transform is performed. For instance, for the frequency characteristic in FIG. 8B, the frequency characteristic of 16 points having the reversed order is added, as shown in FIG. 9. Here, inverse FFT is performed based on Equations (3) and (4), which are to be shown below. In Equations (3) and (4), a value of the frequency characteristic for extracting the grid moiré pattern is denoted by X(n), and a value after FFT is denoted by x(n). In addition, a pixel position is denoted by n, and a pixel size of the image is denoted by N.

$$x(n) = \frac{1}{N}\sum_{n=0}^{N-1} X(n)W^{-kn} \qquad (3)$$

$$W \equiv e^{-j\times(2\pi/N)} = \cos(2\pi/N) - j\times\sin(2\pi/N) \qquad (4)$$

[Step S7]

The FIR filtering section 43 performs FIR filtering on the source image based on the determined FIR filter coefficient. The FIR filtering is performed through reading out the source image stored in the memory 31. The FIR filtering is performed by a given number of coefficients that can achieve effective filtering. For instance, when inverse FFT is performed on the prepared frequency characteristic of 16 points to obtain FIR filter coefficients of 32 points, the FIR filtering is performed using the beginning 15 points. In other words, the FIR filtering is performed using x(0), x(1), x(2), . . . x(14) calculated through Equations (3) and Equation (4) mentioned above. Here in FIG. 10, the FIR filter coefficient is each denoted by f1 through f15.

FIR filtering will be described with reference to FIG. 10. For instance, the FIR filtering is performed on "a15" in the 114th position of the image prior to filtering to obtain "r15" after filtering through the following calculation:

r15=a15×f1+(a14+a16)×f2+(a13+a17)×f3+(a12+a18)×f4+ . . . +(a1+a29)×f15

Here, 15 points are used for the FIR filter coefficients. Similar filtering is performed on other "a16", "a17" and the like. Thus filtering is performed on all pixels horizontally in order for each line from the upper of the image. Thereby, the grid moiré pattern image shown in FIG. 6B is extracted from the source image shown in FIG. 6A.

[Step S8]

Figure 6C:
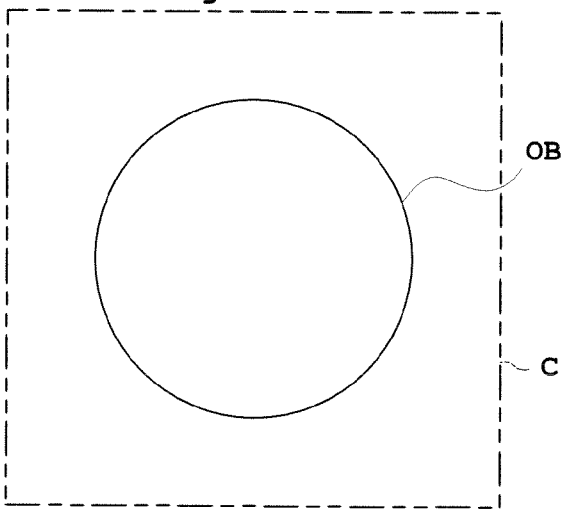
FIG. 6C is a view with respect to explanation of operation of the example showing an image having the grid moiré pattern removed therefrom.

The subtracting section 45 subtracts the extracted grid moiré pattern image from the source image. Thus the grid moiré pattern is removed from the source image. Thereby, as shown in FIG. 6C, an image having the grid moiré patter removed therefrom can be obtained. Thereafter, other necessary processes are performed by the image processor 17 on the image having the grid moiré patter removed therefrom, and then the processed image is displayed on the display unit 21.

According to the X-ray apparatus in the example of this invention with the foregoing configuration, the FFT processor 35 firstly performs one-dimensional FFT to pixels of each horizontal line extracted by the pixel extracting section 33 from the upper of the image containing the grid moiré pattern. Secondary, the peak-frequency detecting section 37 detects a peak frequency from the frequency characteristic for each line calculated through FFT, the peak frequency being a frequency component of the grid moiré pattern. The frequency-characteristic preparing section 39 prepares a frequency characteristic for extracting the grid moiré pattern image in accordance with the peak frequency detected by the peak-frequency detecting section 37. One-dimensional inverse FFT is performed to the prepared frequency characteristic by the inverse FFT processor 41. Thereby an FIR filter coefficient to be used by the FIR filter processor 43 is calculated. Then the FIR filtering section 43 performs FIR filtering on the image containing the grid moiré pattern. Thereby a grid moiré pattern image for removing the grid moiré pattern can be generated.

Accordingly, calculations through one-dimensional FFT and inverse FFT are performed not for the entire of each horizontal line but for a part of each horizontal line. That is, the FFT processor 35 and the inverse FFT processor 41 can perform a reduced calculation amount of FFT and inverse FFT. For instance, when the FPD 3 is formed by 2880×2880 pixels, the foregoing conventional example adopts performance of FFT and inverse FFT to $2^{12}=4096$ data points. However, in the example, FFT is performed to 128 pixels (data points) extracted by the pixel extracting 33. The inverse FFT processor 41 performs inverse FFT for 32 data points (16 points by 2) obtained through adding folded components of the frequency characteristics prepared by the frequency-characteristic preparing section 39. In other words, a reduced calculation amount of FFT and inverse FFT can be achieved. As a result, a reduced calculation amount can be achieved when an image process of extracting a grid moiré pattern image is mounted on hardware, such as FPGA. Thus, an amount of logic and computation time necessary for hardware, such as the FPGA, can be reduced. In addition, the grid moiré pattern image in the entire source image can be extracted through calculating an FIR filter coefficient from a part of pixels extracted in each line and using the coefficient in the FIR filtering.

Moreover, the FFT processor 35 performs one-dimensional FFT to the pixels extracted for each line by the pixel extracting section 33. Consequently, the calculation amount of FFT is not affected by the pixel size.

Moreover, powers-of-two number of data points to undergo FFT or inverse FFT is set, whereby an efficient calculation can be achieved. For instance, where the pixel extracting section 33 extracts 200 pixels for one line, powers-of-two number of data points including the 200 pixels is needed for Fast Fourier Transform and inverse Fast Fourier Transform. That is, $2^8=256$ data points are needed. Thus total 56 data points are needed in addition to the 200 pixels to be extracted.

Moreover, a frequency characteristic prepared by the frequency-characteristic preparing section 39 for extracting the grid moiré pattern is prepared using powers-of-two number of data points. Thereby an efficient calculation can be made upon performance of inverse FFT. In addition, a more reduced calculation amount of inverse FFT can be achieved when a frequency characteristic is prepared using a fewer number of data points than the number of pixels extracted by the image extracting section 33.

Moreover, the X-ray apparatus in the example of this invention includes the subtracting section 45 for removing the grid moiré pattern image extracted by the FIR filter processor 43 from the image. Thereby the grid moiré pattern image containing the grid moiré pattern can be removed from the source image at a higher speed using a grid moiré pattern image extracted at a higher speed due to a reduced calculation amount (computation time) as conventional.

This invention is not limited to the foregoing embodiment, but may be modified as follows.

(1) In the foregoing example of this invention, the image processor 17 performs a process of removing the grid moiré pattern from the source image with the pixel number of the FPD 3, i.e., 2880×2800 pixels in the case of the FPD 3 formed by 2880×2880 pixels. This is not limitative. The image processor 17 includes a binning section (not shown) on an analog-to-digital converter 15 side of the moiré pattern removing section 29 for binning a plurality of pixels to one pixel. That is, the grid moiré pattern is removed from the image having undergone a binning process. In this case, a position of the peak frequency varies upon detection of the peak frequency from the frequency characteristic for each line calculated through FFT. Thus a detection range has to be changed. Here, binning such as binning of 2×2 pixels to one pixel is performed. This binning is performed to the image having 2880× 2880 pixels to obtain an image of 1440×1440 pixels.

(2) The X-ray detector in the foregoing example of this invention is composed by the FPD 3. This is not limitative. For instance, the X-ray detector may be composed of an image intensifier.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An X-ray apparatus with an X-ray irradiation section for irradiating a subject with X-rays, an X-ray detector for detecting X-rays transmitting through the subject, and an X-ray grid disposed on an incidence surface side of the X-ray detector for removing scattered rays, comprising:
   a pixel-extracting section for extracting pixels determined in advance in each line perpendicular to a grid moiré pattern of an image, the grid moiré pattern by the X-ray grid being contained in the image;
   a Fast Fourier Transform processing section for performing one-dimensional Fast Fourier Transform to the pixels extracted by the pixel-extracting section;
   a peak-frequency detecting section for detecting a peak frequency from a frequency characteristic for each line calculated by the Fast Fourier Transform processing section, the peak frequency being a frequency component of the grid moiré pattern;
   a frequency-characteristic preparing section for preparing a frequency characteristic for extracting a grid moiré pattern image in accordance with the peak-frequency;
   an inverse Fast Fourier Transform processing section for performing inverse Fast Fourier Transform to the frequency characteristic prepared by the frequency-characteristic preparing section; and an FIR filtering section for performing FIR filtering on the image with use of a value calculated by the inverse Fast Fourier Transform processing section as an FIR filter coefficient.

2. The X-ray apparatus according to claim 1, wherein the pixel extracting section extracts powers-of-two number of pixels.

3. The X-ray apparatus according to claim 1, wherein the frequency-characteristic preparing section prepares a frequency characteristic using powers-of-two number of data points.

4. The X-ray apparatus according to claim 2, wherein the frequency-characteristic preparing section prepares a frequency characteristic using powers-of-two number of data points.

5. The X-ray apparatus according to claim 1, further comprising:

a subtracting section for removing the grid moiré pattern image extracted by the FIR filtering section from the image.

6. The X-ray apparatus according to claim 2, further comprising:

a subtracting section for removing the grid moiré pattern image extracted by the FIR filtering section from the image.

7. The X-ray apparatus according to claim 3, further comprising:

a subtracting section for removing the grid moiré pattern image extracted by the FIR filtering section from the image.

8. The X-ray apparatus according to claim 4, further comprising:

a subtracting section for removing the grid moiré pattern image extracted by the FIR filtering section from the image.

* * * * *